United States Patent
Nagahashi (10) Patent No.: US 12,383,435 B2
(45) Date of Patent: Aug. 12, 2025

(54) INDIVIDUALLY WRAPPED ABSORBENT ARTICLE

(71) Applicant: DAIO PAPER CORPORATION, Ehime (JP)

(72) Inventor: Ayumi Nagahashi, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 455 days.

(21) Appl. No.: 17/906,384

(22) PCT Filed: Mar. 23, 2021

(86) PCT No.: PCT/JP2021/011965
§ 371 (c)(1),
(2) Date: Sep. 15, 2022

(87) PCT Pub. No.: WO2021/193620
PCT Pub. Date: Sep. 30, 2021

(65) Prior Publication Data
US 2023/0140884 A1    May 11, 2023

(30) Foreign Application Priority Data

Mar. 27, 2020   (JP) ................. 2020-057789

(51) Int. Cl.
*A61F 13/15*    (2006.01)
*A61F 13/60*    (2006.01)

(52) U.S. Cl.
CPC .............. *A61F 13/15* (2013.01); *A61F 13/60* (2013.01)

(58) Field of Classification Search
CPC .. A61F 13/5513; A61F 13/5514; A61F 13/58; A61F 2013/582–583; A61F 13/60
See application file for complete search history.

(56) References Cited

U.S. PATENT DOCUMENTS

| | | | | |
|---|---|---|---|---|
| 5,484,636 A | * | 1/1996 | Berg, Jr. | A61F 15/00 604/389 |
| 5,569,230 A | * | 10/1996 | Fisher | A61F 13/5514 604/389 |
| 6,168,582 B1 | * | 1/2001 | Hasegawa | A61F 13/5514 604/389 |

FOREIGN PATENT DOCUMENTS

| | | |
|---|---|---|
| JP | H10-099370 | 4/1998 |
| JP | 2001-270550 | 10/2001 |

(Continued)

OTHER PUBLICATIONS

International Search Report for PCT/JP2021/011965 mailed on Jun. 8, 2021.

(Continued)

*Primary Examiner* — Michele Kidwell
(74) *Attorney, Agent, or Firm* — IPUSA, PLLC (57) ABSTRACT

[Object] To provide an individually wrapped absorbent article that can be smoothly opened and includes an adhesive tab tape having a sufficient adhesive strength even in a post-process.

[Means of Achieving the Object] An adhesive tab tape 4 includes an upper layer tape 4A and a lower layer tape 4B. The upper layer tape 4A includes an upper layer substrate 20 and an upper layer adhesive 21 that is applied to the lower surface of the upper layer substrate 20. The lower layer tape 4B is removably laminated on the lower side of the upper layer adhesive 21, and includes a lower layer substrate 22 and a lower layer adhesive 23 that is applied to the lower surface of the lower layer substrate 22. The lower layer adhesive 23 of the lower layer tape 4B is disposed on the surface of a folded portion in a rear region $A_B$, and a portion of the lower layer substrate 22 extends across an opening start end 14 from the lower layer adhesive 23 to the surface of a folded portion in a front region $A_F$. This extended (Continued)

portion of the lower layer substrate 22 is non-adhesive. A portion of the upper layer tape 4A, including the upper layer substrate 20 and the upper layer adhesive 21, extends from the lower layer substrate 22 to the surface of the folded portion in the front region.

5 Claims, 10 Drawing Sheets

(56) References Cited

FOREIGN PATENT DOCUMENTS

| JP | 2003-193026 | 7/2003 |
| JP | 2005-102913 | 4/2005 |
| JP | 2013-198586 | 10/2013 |
| WO | 94/14396 | 7/1994 |
| WO | 2010/035648 | 4/2010 |
| WO | 2013/141078 | 9/2013 |

OTHER PUBLICATIONS

Extended European Search Report for 21776238.4 mailed on Jul. 24, 2023.

* cited by examiner

INDIVIDUALLY WRAPPED ABSORBENT ARTICLE

TECHNICAL FIELD

The present invention relates to an individually wrapped absorbent article in which, with an absorbent article such as a sanitary napkin being placed on a wrapping sheet, both end portions in the lengthwise direction of the wrapping sheet are folded toward the center of the wrapping sheet, and an adhesive tab tape is attached to the surface of one folded portion and to the surface of the other folded portion.

BACKGROUND ART

Figure 10:
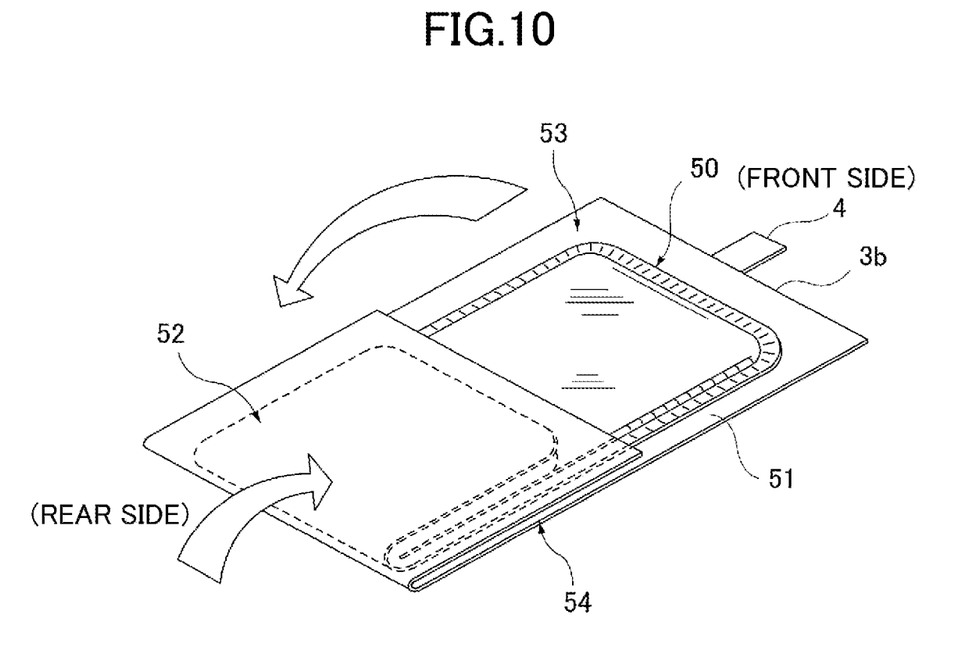
FIG. 10 is a perspective view illustrating a procedure for folding a conventional individually wrapped absorbent article.
Figure 11:
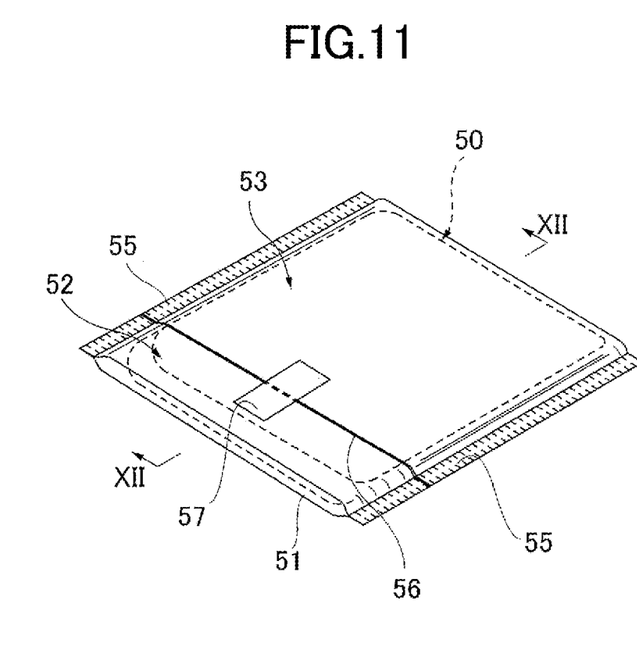
FIG. 11 is a perspective view of the conventional individually wrapped absorbent article.

Conventionally, for example, sanitary napkins are individually wrapped by being tri-folded or quad-folded together with wrapping sheets formed of various film sheets. Specifically, a sanitary napkin that is individually wrapped by being tri-folded together with a wrapping sheet as illustrated in FIG. 10 and FIG. 11 is widely known. In FIG. 10 and FIG. 11, with a sanitary napkin 50 being placed on a wrapping sheet 51 having a rectangular shape, and in this state, a rear region 52 in the lengthwise direction of the wrapping sheet 51 on which the sanitary napkin 50 is placed is folded toward a center region 54 together with the wrapping sheet 51 along a rear folding line, and a front region 53 is folded together with the wrapping sheet 51 along a front folding line such that the front region 53 overlaps with the rear region 52. Then, the open side edge portions of the wrapping sheet are sealed by embossing or the like to form side seal portions 55, 55. Further, the end, which serves as an opening start end 56, in the lengthwise direction of the wrapping sheet 51 is sealed by an adhesive tab tape 57. The adhesive tab tape 57 is attached to both the surface of the front region 53 and the surface of the rear region 52.

When a user uses the sanitary napkin 50, the user pinches the end of the adhesive tab tape 57 attached to the surface of the rear region 52, and completely peels off the adhesive tab tape 57 from the surface of the rear region 52. Then, by further lifting the adhesive tab tape 57, the user lifts the front region 53 of the wrapping sheet 51 from the opening start end 56, and peels the side seal portions 55, 55. After the wrapping sheet 51 is opened, the sanitary napkin 50 is removed from the wrapping sheet 51. Then, the user wears the sanitary napkin 50 by attaching an adhesive layer formed on the non-skin side of the sanitary napkin to the inner surface of underwear.

In general, the wrapping sheet, from which the sanitary napkin has been removed, is used as a disposal sheet for wrapping the used sanitary napkin. In a disposal process, generally, the used sanitary napkin is placed on the wrapping sheet, and in this state, the sanitary napkin is rolled together with the wrapping sheet from one end to the opposite end to which the adhesive tab tape is attached, and the opposite end is sealed by the adhesive tab tape.

As described above, in order to increase the usability of the adhesive tab tape in a post-process, it is desirable for the adhesive tab tape to have a strong adhesive force to maintain the rolled state of the used sanitary napkin. However, if the adhesive force is too strong, the wrapping sheet may be torn when the adhesive tab tape is peeled from the wrapping sheet to open an individually wrapped sanitary napkin. Further, a portion of the torn wrapping sheet may adhere to the adhesive tab tape, and in this case, it may be difficult to re-attach the adhesive tab tape. For the above reasons, the adhesive force of the adhesive tab tape cannot be sufficiently increased.

In order to solve the above-described problem, Patent Document 1 below discloses a tape that includes a first tape and a second tape in which adhesives are applied to the back surfaces of respective substrates. The second tape is removably laminated on the surface of the adhesive of the first tape. With this configuration, it is ensured that the tape can be securely peeled from a wrapping sheet before use and can be re-attached to the wrapping sheet after use.

Further, Patent Document 2 below discloses a structure in which an absorbent article is placed on a wrapping sheet, and in this state, both end portions in the lengthwise direction of the wrapping sheet are folded toward the center of the wrapping sheet such that one end portion overlaps with the other end portion. Further, an adhesive tape is attached from the surface of the one end portion to the surface of the other end portion. Further, both edge portions in the widthwise direction of the wrapping sheet are sealed. In this structure, at least a part of the one end portion of the wrapping sheet where the adhesive tape is attached is constituted by a double sheet.

RELATED-ART DOCUMENTS

Patent Documents

Patent Document 1: Japanese Laid-open Patent Publication No. 2001-270550

Patent Document 2: Japanese Laid-open Patent Publication No. 2005-102913

SUMMARY OF THE INVENTION

Problem to be Solved by the Invention

Figure 12:
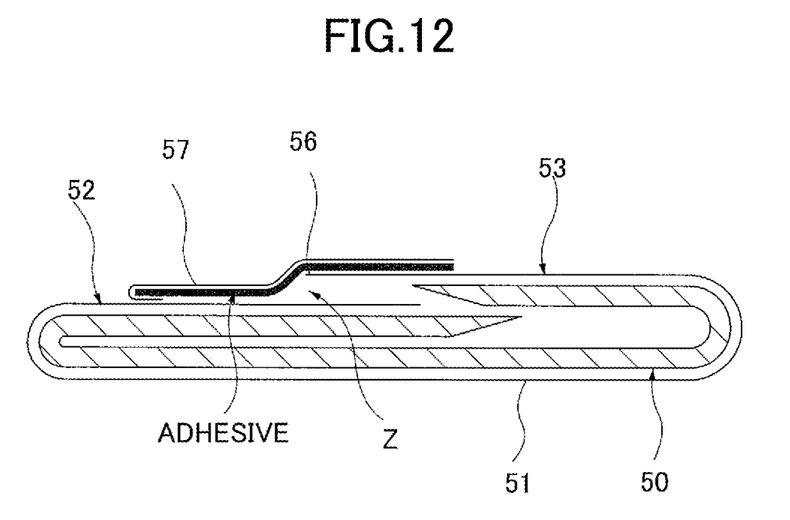
FIG. 12 is a cross-sectional view of the conventional individually wrapped absorbent article taken through XII-XII of FIG. 11.

However, in conventional adhesive tab tapes as described in Patent Documents 1 and 2 above, as illustrated in FIG. 12, an adhesive is applied from the surface of the front region 53 to the surface of the rear region 52, which are folded to individually wrap the sanitary napkin. Therefore, the adhesive may leak into an area (denoted as Z in the drawing) located between the front region 53 and the rear region 52 of the wrapping sheet 51 and under the opening start end 56. If the adhesive leaks into the area, the front region 53 and the rear region 52 of the wrapping sheet 51 may adhere to each other, thus preventing the smooth opening of the individually wrapped sanitary napkin.

If the amount of an adhesive applied is reduced in order to prevent leakage of an adhesive, or if an adhesive having a low adhesive force is used in order to enable smooth opening of the individually wrapped sanitary napkin even when an adhesive leaks, the adhesive force of a tape may become reduced when the tape is re-used in a post-process, and thus, it may be difficult to re-attach the tape.

In view of the above, it is an object of the present invention to provide an individually wrapped absorbent article that can be smoothly opened and includes an adhesive tab tape having a sufficient adhesive strength even in a post-process.

Means to Solve the Problem

In order to solve the above-described problem, in a first aspect, an individually wrapped absorbent article that includes an absorbent article, a wrapping sheet, and an adhesive tab tape is provided. With the absorbent article being placed on the wrapping sheet, both end portions in a lengthwise direction of the wrapping sheet are folded toward a center of the wrapping sheet such that one folded portion overlaps with the other folded portion and an end of the one folded portion serves as an opening start end, and an adhesive tab tape is attached to a surface of the one folded portion and a surface of the other folded portion. The adhesive tab tape includes an upper layer tape and a lower layer tape. The upper layer tape includes an upper layer substrate and an upper layer adhesive that is applied to a lower surface of the upper layer substrate. The lower layer tape is removably laminated on a lower side of the upper layer adhesive and includes a lower layer substrate and a lower layer adhesive that is applied to a lower surface of the lower layer substrate. The lower layer adhesive of the lower layer tape is disposed on the surface of the other folded portion, and a portion the lower layer substrate extends across the opening start end from the lower layer adhesive to the surface of the one folded portion. The portion of the lower layer substrate is non-adhesive. A portion of the upper layer tape, including the upper layer substrate and the upper layer adhesive, extends from the lower layer substrate to the surface of the one folded portion.

In the above-described first aspect, the adhesive tab tape attached to the wrapping sheet includes the upper layer tape and the lower layer tape that is removably laminated on the lower side of the upper layer adhesive. While the lower layer adhesive of the lower layer tape is disposed only on the surface of the other folded portion and does not extend to the surface of the one folded portion, a portion of the lower layer substrate extends across the opening start end from the lower layer adhesive to the surface of the one folded portion. This extended portion of the lower layer substrate is non-adhesive. Further, while the upper layer tape including the upper layer substrate and the upper layer adhesive removably covers the surface of the lower layer substrate, a portion of the upper layer tape extends from the lower layer substrate to the surface of the one folded portion. As described, the lower layer adhesive of the lower layer tape is not disposed across the opening start end. In addition, the opening start end is covered by the lower layer substrate such that the upper layer adhesive of the upper layer tape does not directly contact the opening start end. Accordingly, the one folded portion and the other folded portion can be prevented from adhering to each other at the opening start end due to leakage of an adhesive, thereby facilitating the smooth opening of the individually wrapped absorbent article from the opening start end.

When a user opens the individually wrapped absorbent article and removes the absorbent article, the user pinches the end on the other folded portion side of the upper layer tape, and completely peels off the upper layer tape from the lower layer tape. Then, by further lifting the upper layer tape, the user lifts the one folded portion of the wrapping sheet from the opening start end, and peels the side seal portions to open the individually wrapped absorbent article. Then, the user removes the sanitary napkin from the wrapping sheet. In a state in which the absorbent article is removed, the lower layer tape remains attached to the surface of the other folded portion, and the upper layer adhesive of the upper layer tape, which has been peeled from the lower layer substrate, is being exposed.

Accordingly, even if the adhesive force of the upper layer adhesive of the upper layer tape is increased, the wrapping sheet can be smoothly unfolded without being torn. In addition, even in a post-process, a sufficient adhesion strength can be ensured by the exposed upper layer adhesive.

In a second aspect, the individually wrapped absorbent article according to claim 1 is provided. The separating distance between the lower layer adhesive and the opening start end is 2 mm to 8 mm.

In the second aspect, the separating distance between the lower layer adhesive and the opening start end is specified so as to avoid contact between the lower layer adhesive and the opening start end. Accordingly, the one folded portion and the other folded portion can be prevented from adhering to each other.

In a third aspect, the individually wrapped absorbent article according to claim 1 or 2 is provided. The length to which a portion of the lower layer substrate extends from the opening start end to the surface of the one folded portion is 2 mm to 5 mm.

In the third aspect, the length to which a portion of the lower layer substrate extends from the opening start end to the surface of the one folded portion is specified, so as to prevent the one folded portion and the other folded portion from adhering to each other due to leakage of the upper layer adhesive to the opening start end.

In a fourth aspect, the individually wrapped absorbent article according to any one of claims 1 to 3 is provided. The length to which the portion of the upper layer tape extends from the lower layer substrate to the surface of the one folded portion is 10 mm to 30 mm.

In the fourth aspect, the length of the portion of the upper layer tape that is attached to the wrapping sheet is specified. The length is required to lift the upper layer tape and peel the one folded portion from the opening start end.

In a fifth aspect, the individually wrapped absorbent article according to any one of claims 1 to 4 is provided. An end on the other folded portion side of the upper layer tape extends beyond the lower layer tape, and the end of the upper layer tape is non-adhesive.

In the fifth aspect, in order for the user to readily pinch the end of the upper layer tape when opening the individually wrapped absorbent article, a pinch portion is formed at the end on the other folded portion side of the upper layer tape. The pinch portion extends beyond the lower layer tape and is non-adhesive.

Effects of the Invention

As described above in detail, according to the present invention, an individually wrapped absorbent article, that can be smoothly opened and includes an adhesive tab tape having a sufficient adhesive strength even in a post-process, can be provided.

BRIEF DESCRIPTION OF THE DRAWINGS

FIG. 8 (A) through FIG. 8 (C) are perspective views illustrating an opening procedure;

MODE FOR CARRYING OUT THE INVENTION

In the following, embodiments of the present invention will be described in detail with reference to the accompanying drawings.

[Individually Wrapped Sanitary Napkin N]

Figure 1:
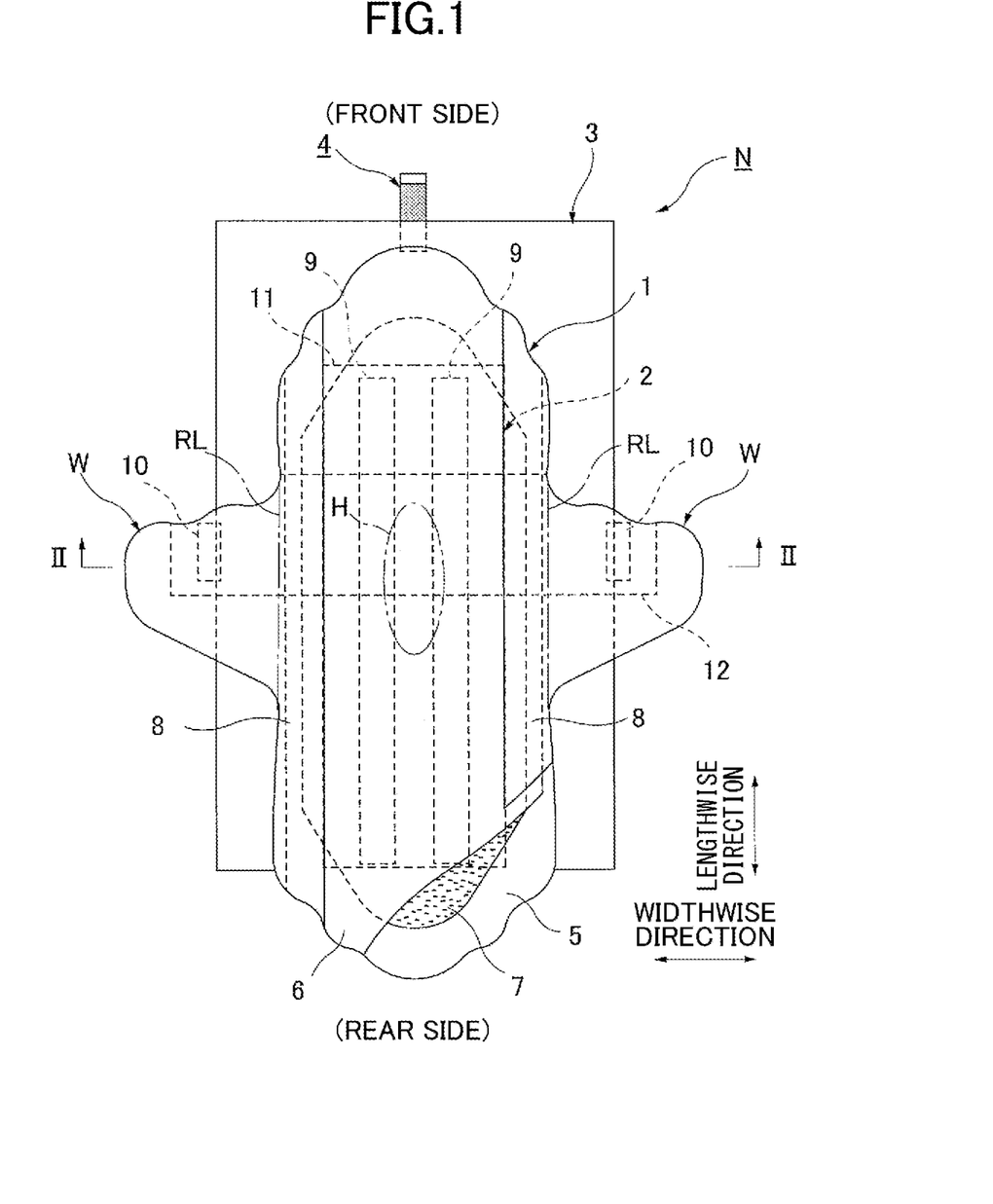
FIG. 1 is a partially expanded cutaway view of an individually wrapped sanitary napkin N according to the present invention.
Figure 2:
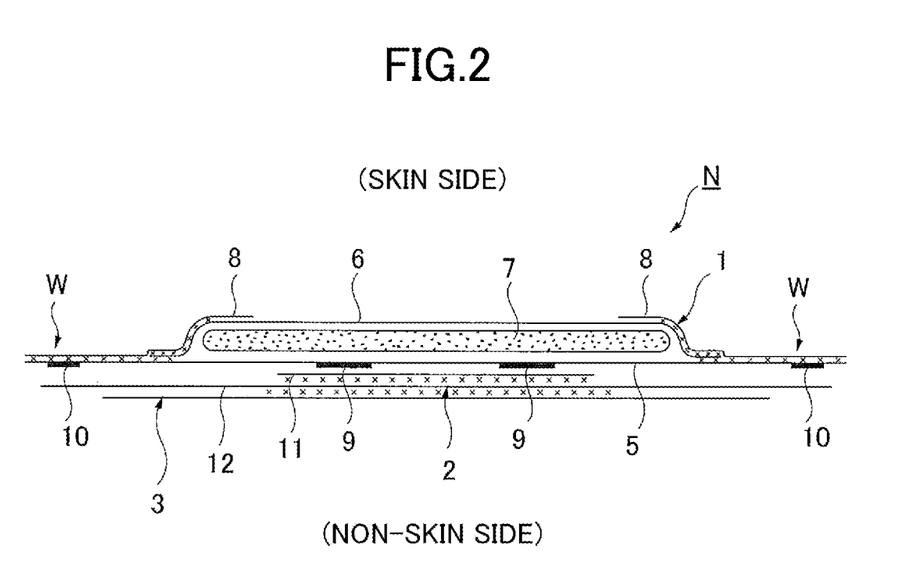
FIG. 2 is a cross-sectional view of the individually wrapped sanitary napkin N taken through II-II of FIG. 1.
Figure 3:
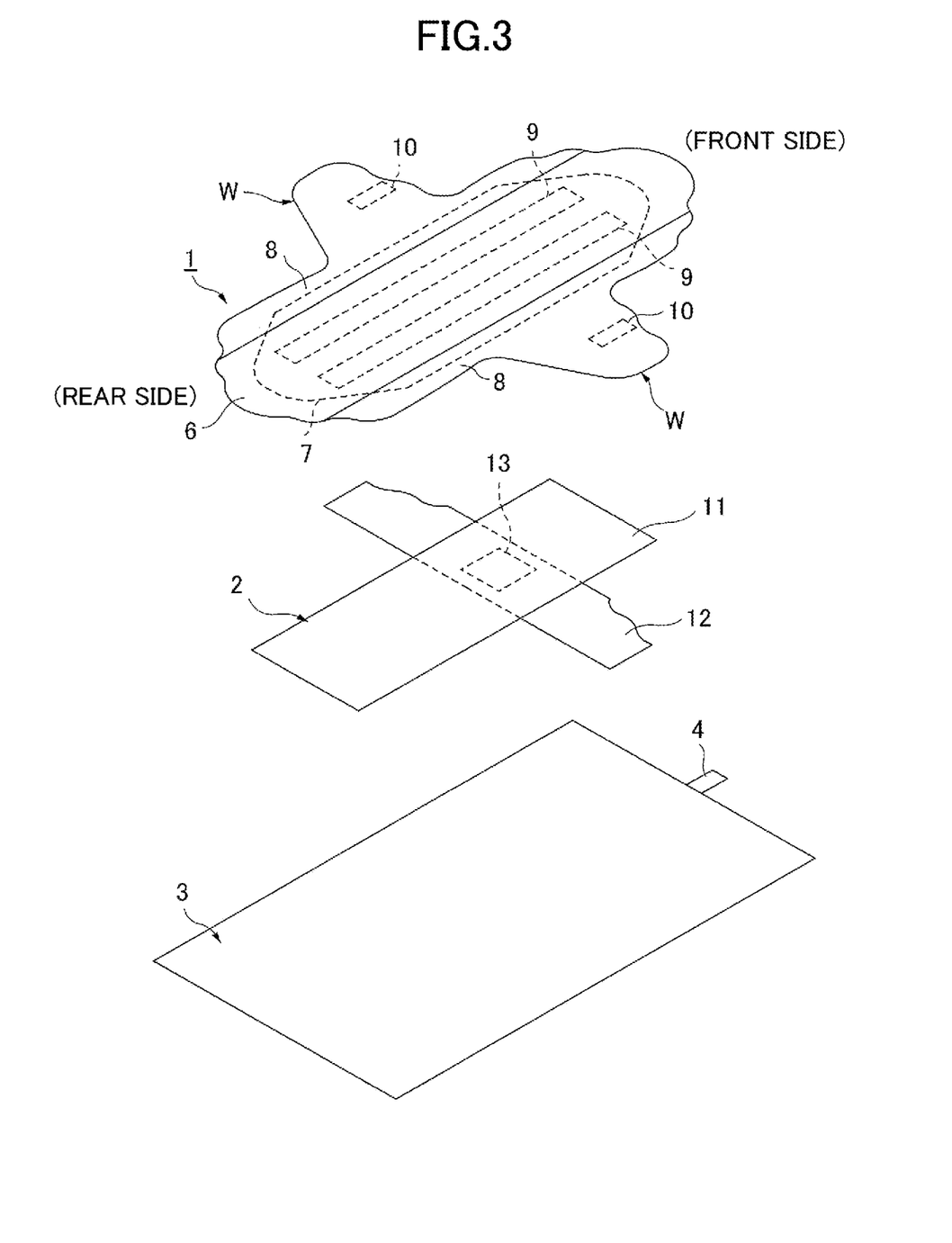
FIG. 3 is an exploded perspective view of the individually wrapped sanitary napkin N that is unfolded.

As illustrated in FIG. 1 through FIG. 3, an individually wrapped sanitary napkin N according to the present invention includes a sanitary napkin 1, a peeling sheet 2 configured to cover displacement-preventing adhesive layers of the sanitary napkin 1, a wrapping sheet 3 configured to individually wrap the sanitary napkin 1, and an adhesive tab tape 4 configured to seal the opening start end of the wrapping sheet 3 and to extend across the opening start end. In this specification, a sanitary napkin is described as an example of an absorbent article; however, the present invention can be applied to any absorbent article such as a panty liner or an incontinence pad.

[Sanitary Napkin 1]

As illustrated in FIG. 1 through FIG. 3, the sanitary napkin 1 includes a liquid-impermeable back sheet 5 formed of a polyethylene sheet or the like, a liquid-permeable top sheet 6 that allows menstrual blood, vaginal discharge, and the like (hereinafter may be collectively referred to as body fluids) smoothly pass through, an absorbent body 7 disposed between the top sheet 6 and the back sheet 5 and formed of, for example, cotton pulp or synthetic pulp, and side sheets 8, 8 provided on the lateral sides of a skin-contact surface and extending along substantially the entire length in the lengthwise direction of the sanitary napkin 1. At the periphery of the absorbent body 7, the outer edges of the back sheet 5 and the top sheet 6 are bonded to each other with an adhesive such as a hot melt or an adhesive means such as a heat seal and an ultrasonic seal. Further, at side edges of the absorbent body 7, portions of the back sheet 5 and the side sheets 8 that laterally extend longer than the absorbent body 7 are bonded to each other with an adhesive such as a hot melt or by an adhesive means such as a heat seal and an ultrasonic seal. As a result, flaps without the absorbent body are formed. Although not illustrated, in order to maintain the shape of the absorbent body 7 and to improve diffusivity thereof, the absorbent body 7 may be surrounded by an encapsulating sheet formed of crepe paper or a non-woven fabric. Further, a second sheet formed of a hydrophilic non-woven fabric and having approximately the same shape as the top sheet 6 may be disposed on the non-skin side of the top sheet 6.

In the following, the structure of the sanitary napkin 1 will be described in more detail. The back sheet 5 uses a sheet material such as polyethylene having at least a water shielding property. In addition, from the viewpoint of preventing stuffiness, it is desirable to use a sheet material having moisture permeability. As such a water shielding and moisture permeable sheet material, a microporous sheet is preferably used. The microporous sheet may be obtained by melt-kneading an inorganic filler into an olefinic-based resin such as polyethylene or polypropylene to form a sheet, followed by stretching the sheet in a monoaxial or a biaxial direction. As the back sheet 5, a polyethylene laminate non-woven fabric having a plastic film and a non-woven fabric layered on each other may be used. A plurality of, in the illustrated example, two body displacement-preventing adhesive layers 9, 9 are formed on the non-skin side (outer side) of a main body part of the back sheet 5 where the absorbent body 7 is placed. The body displacement-preventing adhesive layers 9, 9 are disposed along the lengthwise direction of the sanitary napkin 1, and secure the sanitary napkin 1 to underwear when worn.

Next, as the top sheet 6, a porous or non-porous non-woven fabric or a porous plastic sheet is preferably used. As material fibers constituting the non-woven fabric, for example, olefins such as polyethylene and polypropylene; regenerated fibers such as rayon and cuprammonium rayon; and natural fibers such as cotton can be used alone or in combination. A non-woven fabric obtained by an appropriate processing method such as a span lace method, a spunbond method, a thermal bond method, a melt-blown method, a needle punch method, or the like can be used. Among these processing methods, the span lace method is preferable in terms of flexibility and draping characteristics, and the thermal bond method is preferable in terms of bulkiness and compression restoration. If a large number of through holes are formed in the top sheet 6, the sanitary napkin can quickly absorb body fluids and its dry touch property can be improved. Although either long fibers or short fibers may be used for the nonwoven fabric, short fibers are preferably used to provide a texture of a towel cloth. Further, in order to facilitate embossing, olefin-based fibers such as polyethylene or polypropylene having a relatively low melting point may be used. Further, composite fibers such as core-in-sheath fibers having high-melting-point fibers as a core and low-melting-point fibers as a sheath, side-by-side fibers, or split fibers may be preferably used.

The absorbent body 7 interposed between the back sheet 5 and the top sheet 6 may be formed of, for example, cotton-like pulp and a water absorbent polymer. The water absorbent polymer may be mixed, for example, as a granular powder, into the pulp that forms the absorbent body. Examples of the pulp include chemical pulp made from wood, cellulose fibers such as dissolving pulp, and synthetic cellulose fibers such as rayon and acetate. In terms of function and price, softwood pulp with a long fiber length is more preferably used than hardwood pulp. If crepe paper (not illustrated) for enveloping the absorbent body 7 is provided, the crepe paper is interposed between the top sheet 6 and the absorbent body 7. Therefore, the crepe paper having high absorbency can quickly diffuse body fluids while also preventing backflow of body fluids.

Further, synthetic fibers may also be mixed with the absorbent body 7. Examples of the synthetic fibers include polyolefins such as polyethylene and polypropylene, polyesters such as polyethylene terephthalate, and polybutylene terephthalate, polyamides such as nylon, and copolymers thereof. Among these, two kinds of the synthetic fibers may be used in combination. Further, composite fibers such as core-in-sheath fibers having high-melting-point fibers as a core and low-melting-point fibers as a sheath, split type fibers, and the like may be used. Alternatively, if hydrophobic fibers are used, the hydrophobic fibers may be surface-treated with a hydrophilic agent to confer affinity to body fluids.

As illustrated in a cross-sectional view of FIG. 2, the width of the top sheet 6 is slightly larger than the width of the absorbent body 7 so as to cover the absorbent body 7. The side sheets 8 that are different from the top sheet 6 are provided outside the absorbent body 7. The side sheets 8 are formed of a non-woven fabric material to which appropriate water-repellency treatment or hydrophilic treatment is applied, depending on the purpose such as preventing penetration of body fluids or enhancing texture. For example, if preventing penetration of body fluids or enhancing texture is given priority, a water-repellent non-woven fabric coated with a silicone-based, a paraffin-based, or an alkyl-chromic-chloride-based water-repellent agent is desirably used. If the absorbency of body fluids is given priority, a hydrophilic non-woven fabric is preferably used. Such a hydrophilic nonwoven fabric may be prepared by polymerizing a compound having a hydrophilic group such as an oxidation product of polyethylene glycol during a production process of synthetic fibers, or by processing synthetic fibers with metal salt such as stannic chloride to partially dissolve the surfaces of the synthetic fibers and give them porosity, and depositing metal hydroxide on the synthetic fibers. The resulting synthetic fibers become swollen or porous and exhibit a hydrophilic property due to capillary action. As the side sheets 8, sheets that use synthetic fibers or regenerated fibers as a material and is formed by an appropriate processing method may be used. Preferably, a non-woven fabric having air permeability with a reduced basis weight may be used.

As illustrated in FIG. 2, on an outer side of the sanitary napkin relative to the middle portion in the width direction, each of the side sheets 8 is bonded from a predetermined inward position to the outer edge of the back sheet 5 with an adhesive such as a hot-melt adhesive. The layered sheet portions of the back sheet 5 and the side sheets 8 form flaps on both sides of the absorbent body 7, without the absorbent body 7 being interposed. The flaps may include a pair of right and left wing-shaped flaps W, W at positions alongside a body fluid excretion orifice corresponding region H. Wing displacement-preventing adhesive layers 10 are provided on the outer surfaces of the respective wing-shaped flaps W. When the sanitary napkin is attached to underwear, the wing-shaped flaps W are folded back along fold-back lines RL so as to be fixed to a crotch portion of the underwear.

Examples of a suitable adhesive for the displacement-preventing adhesive layers 9 and 10 include a styrene-based polymer, a tackifier, a plasticizer, and a combination thereof. Examples of the styrene-based polymer include a styrene-ethylene-butylene-styrene block copolymer, a styrene-butylene-styrene block copolymer, a styrene-isobutylene-styrene copolymer, a styrene-butadiene-styrene block copolymer, and the like. One of the above-described copolymers may be used alone or two or more of the above-described copolymers may be used as a polymer blend. Among these, a styrene-butadiene-styrene block copolymer is preferably used from the viewpoint of thermostability. Further, as the tackifier and the plasticizer, materials that are solid at room temperature may be preferably used. Examples of the tackifier include C5-based petroleum resins, C9-based petroleum resins, dicyclopentadiene-based petroleum resins, rosin-based petroleum resins, polyterpene resins, terpenephenol resins, and the like. Examples of the plasticizer include monomer plasticizers such as trifrecyl phosphate, dibutyl phthalate, and dioctyl phthalate, as well as polymer plasticizers such as vinyl polymers and polyesters.

[Peeling Sheet 2]

The peeling sheet 2 may preferably include a body peeling sheet 11 configured to removably cover the entire body displacement-preventing adhesive layers 9, 9, and a wing peeling sheet 12 configured to removably cover the entire wing displacement-preventing adhesive layers 10, 10. However, the peeling sheet 2 may be a single sheet constituted by the body peeling sheet 11 and the wing peeling sheet 12. The wing peeling sheet 12 traverses the width of the body peeling sheet 11, extends to a predetermined position located forward of the wing-shaped flaps W, and the outer periphery of the wing peeling sheet 12 is cut following the peripheral edge of the sanitary napkin. As illustrated in FIG. 3, the peeling sheets 11 and 12 are unremovably bonded by a bonding portion 13 that is formed in an overlapping portion of the peeling sheets 11 and 12. Further, the peeling sheets 11 and 12 are bonded to the wrapping sheet 3. The peeling sheets 11 and 12 are configured to be peeled off from the displacement-preventing adhesive layers 9 and 10 together with the wrapping sheet 3 when the sanitary napkin 1 is removed from the wrapping sheet 3.

As the peeling sheets 11 and 12, paper or plastic sheets subjected to mold-release treatment may be used. The mold-release treatment may be applied by coating or spraying a mold-release agent such as silicone-based resin, fluorine-based resin, or tetrafluoroethylene-based resin onto the surfaces of the peeling sheets 11 and 12 contacting the displacement-preventing adhesive layers 9 and 10. In this case, at least for the wing peeling sheet 12, a plastic sheet with high flexibility may be used to smoothly unfold the wing flaps W, W when the package is opened and the wrapping sheet is peeled. Note that films or non-woven fabrics may be used without any special mold-release treatment as long as the adhesion does not substantially decrease.

[Wrapping Sheet 3]

As the wrapping sheet 3, a sheet-shaped member having a rectangular shape is used as illustrated in FIG. 1 and FIG. 3. Specifically, a polyolefin-based film such as polypropylene or polyethylene, a film such as polyester or polyvinyl alcohol, a non-woven fabric, paper, a polyethylene laminate non-woven fabric, or the like may be used. A film is preferably used if a design by printing is given priority. A non-woven fabric is preferably used if a texture, soft feel, and the like are given priority.

As illustrated in FIG. 1 and FIG. 3, the wrapping sheet 3 has a length such that at least the front edge of the wrapping sheet 3 is located forward of the front edge of the sanitary napkin 1. Further, as illustrated in FIG. 4, the wrapping sheet 3 has a width such that the width of the wrapping sheet 3 is slightly larger than the width of the sanitary napkin 1 with the wing-shaped flaps W, W being folded inward along folding lines RL, RL.

[Overview of Individually Wrapping Sanitary Napkin]

Figure 4:
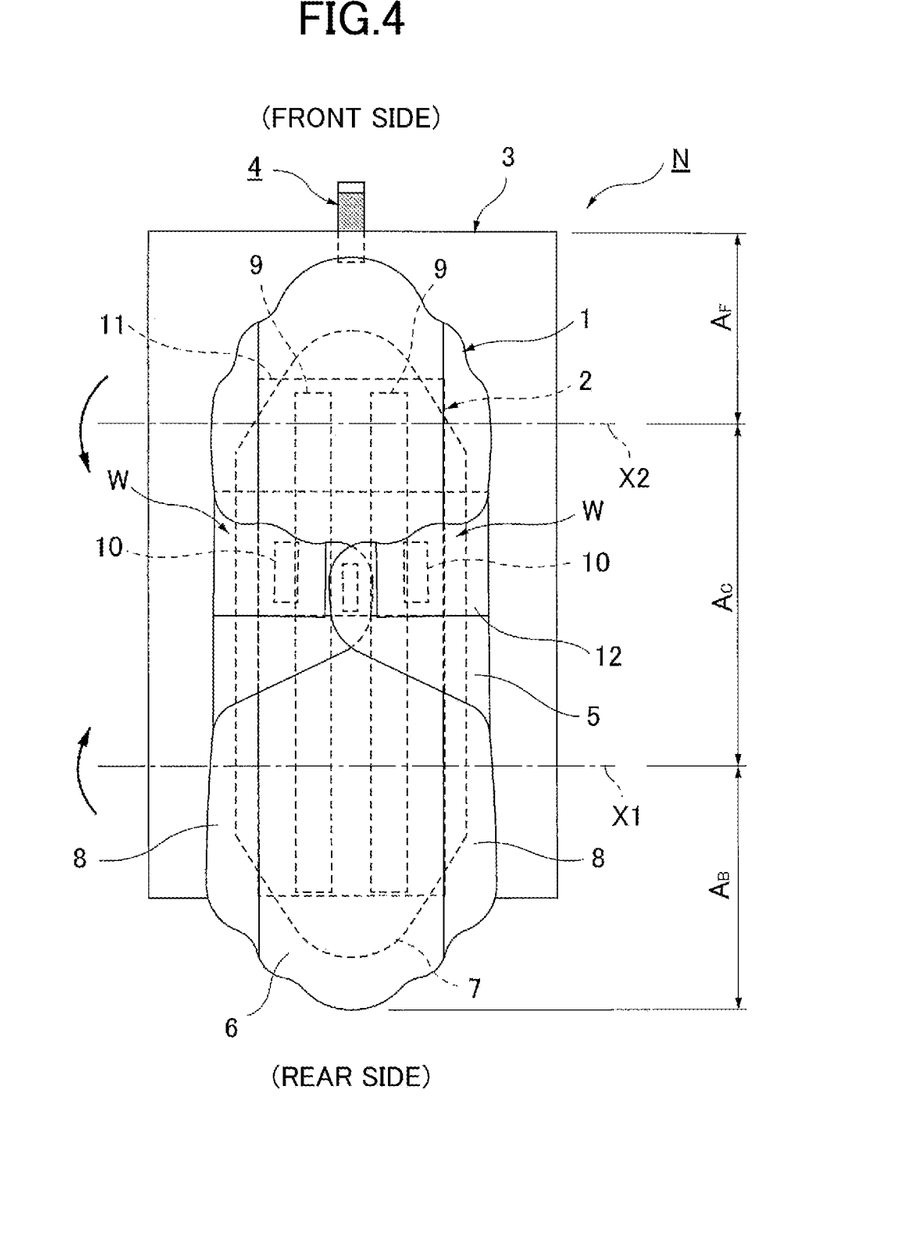
FIG. 4 is a plan view illustrating a procedure for folding the individually wrapped sanitary napkin N.
Figure 5:
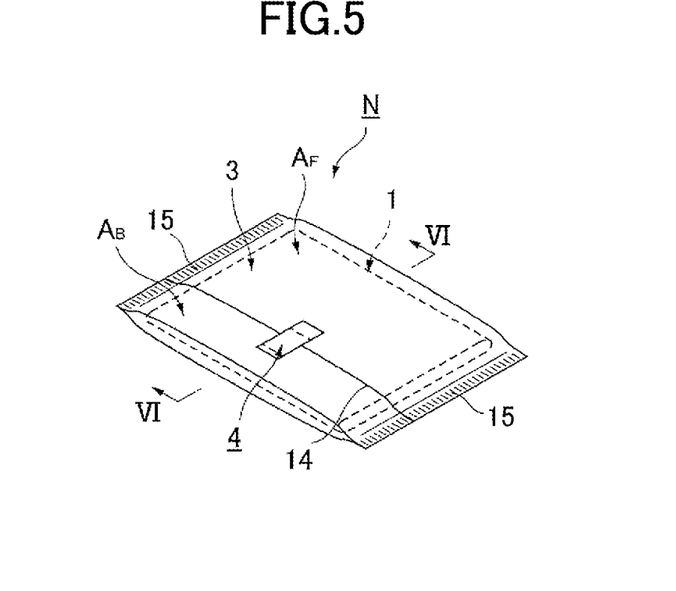
FIG. 5 is a perspective view of the individually wrapped sanitary napkin N.

In order to individually wrap the sanitary napkin 1 in the wrapping sheet 3, as illustrated in FIG. 4, the sanitary napkin 1, the peeling sheet 2, and the wrapping sheet 3 are laminated such that the peeling sheet 2 bonded to the wrapping sheet 3 covers the displacement-preventing adhesive layers 9 and 10. In the actual manufacturing process, the displacement-preventing adhesive layers 9 and 10 are applied to the surface (on which the sanitary napkin is placed) of the peeling sheet 2, and subsequently the sanitary napkin 1 is placed on the surface of the peeling sheet 2. In this manner, the displacement-preventing adhesive layers 9 and 10 are transferred to the back sheet 5 of the sanitary napkin 1. Next, as illustrated in FIG. 4, a rear region $A_B$ of the sanitary napkin 1 is folded toward a center region $A_C$ together with the wrapping sheet 3 along a folding line X1, which extends in the widthwise direction. Then, a front region $A_F$ of the sanitary napkin 1 is folded together with the wrapping sheet 3 along a folding line X2, which extends in the widthwise direction, such that the front region $A_F$ overlaps with the folded rear region $A_B$. In this manner, the sanitary napkin 1 is tri-folded. Subsequently, as illustrated in FIG. 5, side seal portions 15, 15 are formed at both open side edge portions of the wrapping sheet 3 by one or a combination of appropriate sealing means such as embossing, heating, or an adhesive. Further, the center in the widthwise direction of the wrapping sheet 3, that is, the center at the end (an opening start end 14) in the lengthwise direction of the wrapping sheet 3 is sealed by the adhesive tab tape 4. The adhesive tab tape 4 extends in a direction perpendicular to the extending direction of the opening start end 14, and is attached to a folded portion of the wrapping sheet 3 in the front region $A_F$ and to a folded portion of the wrapping sheet 3 in the rear region $A_B$. In this manner, the individually wrapped sanitary napkin N is obtained.

[Adhesive Tab Tape 4]

Figure 6:
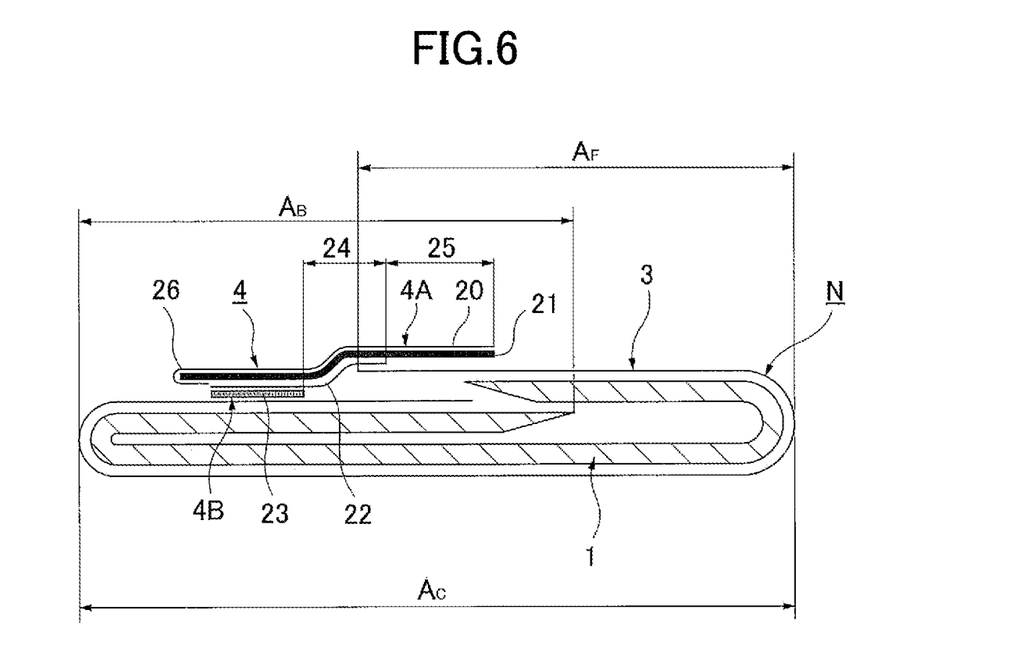
FIG. 6 is a cross-sectional view of the individually wrapped sanitary napkin N taken through VI-VI of FIG. 5.
Figure 7:
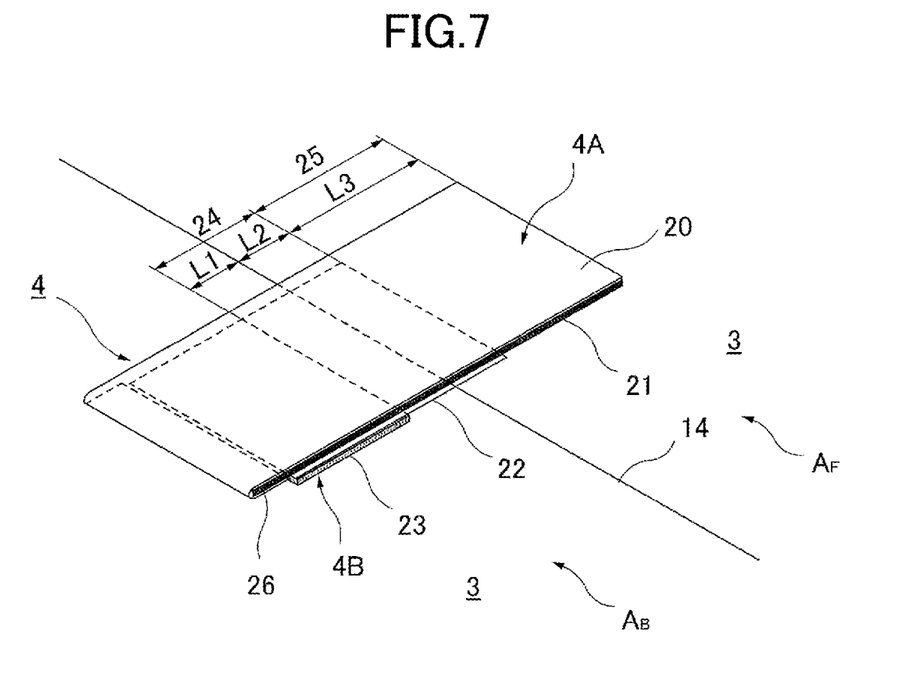
FIG. 7 is an enlarged perspective view of an adhesive tab tape 4.

As illustrated in FIG. 6 and FIG. 7, the adhesive tab tape 4 includes an upper layer tape 4A and a lower layer tape 4B. The upper layer tape 4A includes an upper layer substrate 20 and an upper layer adhesive 21 that is applied to the lower surface of the upper layer substrate 20. The lower layer tape 4B is removably laminated on the lower side of the upper layer adhesive 21, and includes a lower layer substrate 22 and a lower layer adhesive 23 that is applied to the lower surface of the lower layer substrate 22.

As illustrated in FIG. 6 and FIG. 7, the lower layer adhesive 23 of the lower layer tape 4B is disposed only on the surface of the folded portion of wrapping sheet 3 in the rear region $A_B$. In addition, a portion of the lower layer substrate 22 extends across the opening start end 14 from the lower layer adhesive 23 to the surface of the folded portion of the wrapping sheet 3 in the front region $A_F$. This portion (extended portion 24) of the lower layer substrate 22 is a non-adhesive portion that has no adhesive on its bottom surface and is not bonded to any member. The lower layer adhesive 23 is unremovably attached to the folded portion of the wrapping sheet 3 in the rear region $A_B$. Providing the lower layer adhesive 23 only on the surface of the folded portion of the wrapping sheet 3 in the rear region $A_B$ means that the lower layer adhesive 23 does not extend across the opening start end 14 to the surface of the folded portion of the wrapping sheet 3 in the front region $A_F$.

The upper layer substrate 20 and the upper layer adhesive 21 of the upper layer tape 4A removably cover the surface of the lower layer substrate 22. Further, a portion of the upper layer tape 4A extends from the lower layer substrate 22 to the surface of the folded portion of the wrapping sheet 3 in the front region $A_F$, and this portion (extended portion 25) of the upper layer tape 4A is attached to the surface of the wrapping sheet 3. While the upper layer tape 4A is removably attached to the lower layer substrate 22, the extended portion 25 of the upper layer tape 4A, which extends beyond from the lower layer substrate 22, is unremovably attached to the surface of the folded portion of the wrapping sheet 3 in the front region $A_F$.

As used herein, the term "removably" means that an adhesive can be peeled from the contact surface of an underlying member by a peeling force when a user pinches and pulls the adhesive tab tape 4 with the finger to open the individually wrapped sanitary napkin N. Further, the term "unremovably" means that an adhesive cannot be peeled from the contact surface of an underlying member by a peeling force when a user pinches and pulls the adhesive tab tape 4 with the finger to open the individually wrapped sanitary napkin N.

As described above, in the adhesive tab tape 4 of the individually wrapped sanitary napkin N according to the present invention, the lower layer adhesive 23 of the lower layer tape 4B, attached to the folded portion in the rear region $A_B$, does not extend across the opening start end 14 to the folded portion in the front region $A_F$. In addition, the opening start end 14 is covered by the lower layer substrate 22 such that the upper layer adhesive 21 of the upper layer tape 4A does not directly contact the opening start end 14. Accordingly, the folded portion of the wrapping sheet 3 in the front region $A_F$ can be prevented from adhering to the folded portion of the wrapping sheet 3 in the front region $A_F$ due to leakage of an adhesive. Thus, the individually wrapped sanitary napkin N can be smoothly opened from the opening start end 14.

Each of the upper layer tape 4A and the lower layer tape 4B is formed in a substantially rectangular shape, and has the substantially same dimension in the widthwise direction. With respect to a dimension in the lengthwise direction, both ends of the upper layer tape 4A extend beyond both ends of the lower layer tape 4B. The upper layer adhesive 21 of the upper layer tape 4A is removably attached to the surface of the lower layer substrate 22 of the lower layer tape 4B. Specifically, the upper layer tape 4A is laminated and held on and the lower layer tape 4B. That is, the adhesive tab tape 4 has a double tape structure in which the upper layer tape 4A and the lower layer tape 4B are laminated at an intermediate portion in the lengthwise direction of the adhesive tab tape. Further, the adhesive tab tape 4 is configured such that one end in the lengthwise direction of the upper layer tape 4A extends beyond the lower layer tape 4B Each of the upper layer substrate 20 and the lower layer substrate 22 may be formed of a plastic film, a non-woven fabric, a polyethylene laminate non-woven fabric, paper, or a composite material thereof. The surface of the lower layer substrate 22, which contacts the upper layer adhesive 21, may be subjected to mold-release treatment by coating or spraying a mold-release agent such as silicone-based resin, fluorine-based resin, or tetrafluoroethylene-based resin. However, a film or a non-woven fabric without being subjected to any special mold-release treatment is preferably used as long as the upper layer adhesive 21 does not substantially cause a decrease in adhesion.

As each of the upper layer adhesive 21 and the lower layer adhesive 23, an adhesive having a two-phase block structure of styrene and rubber phases obtained by mixing an adhesive base agent such as a styrene block polymer, a tackifier, a softening agent, and an antioxidant can be used. Examples of the styrene block polymer include SEBS, SIS, SBS, and SPS. Examples of the tackifier include a C5-based petroleum resin, a C9-based petroleum resin, a C5/C9-based petroleum resin, a polyterpene resin, which is a copolymer of α-pinene, β-pinene, or dipentene, a rosin-based resin, and a hydrogenated product thereof, which have a softening point of 80° C. or more and a molecular weight of 400 to 2000. Examples of the softening agent include a processing oil, various types of plasticizers, polybutene, and a liquid resin, which have a softening point of 10° C. or more and an average molecular weight of 200 to 700.

Figure 8:
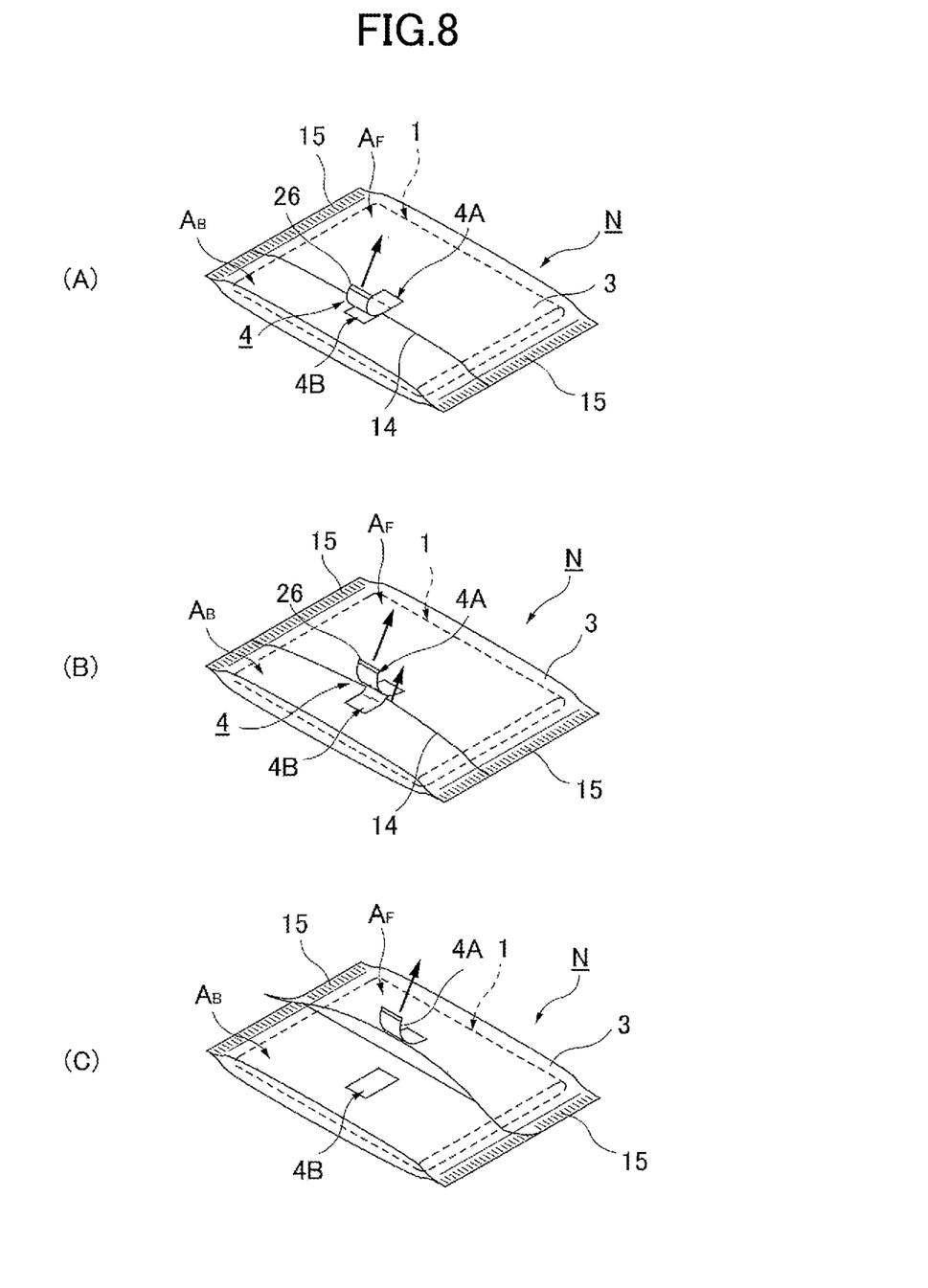

In a procedure for opening the individually wrapped sanitary napkin N, first, as illustrated in FIG. 8 (A), the end of the upper layer tape 4A, located in the rear region $A_B$, is pinched and lifted, and the upper layer tape 4A is completely peeled off from the lower layer tape 4B. Next, as illustrated in FIG. 8 (B), when the upper layer tape 4A is further lifted, the center at the opening start end 14 is lifted and a gap is formed between the opening start end 14 and the surface of the folded portion in the rear region $A_B$. In addition, the extended portion 24, which extends across the opening start end 14 to the folded portion of the wrapping sheet 3 in the front region $A_F$, is lifted. Subsequently, when the upper layer tape 4A is further lifted, a state in which the extended portion 24 of the lower layer substrate 22 extends across the opening start end 14 to the folded portion of the wrapping sheet 3 in the front region $A_F$ is changed to a state in which the extended portion 24 of the lower layer substrate 22 is placed on the surface of the folded portion in the rear region $A_B$, as illustrated in FIG. 8 (C). Subsequently, by further lifting the upper layer tape 4A, the side seal portions 15, 15 in the front region $A_F$ are peeled, and the folded portion in the front region AF is unfolded. Then, the rear end of the sanitary napkin 1 is pinched to peel the side seal portions 15, 15 in the rear region $A_B$. After the folded portion of the wrapping sheet 3 in the rear region $A_B$ is unfolded, the sanitary napkin 1 is peeled from the peeling sheet 2 and removed.

With the individually wrapped sanitary napkin N being opened, the lower layer tape 4B remains fixed to the surface of the folded portion of the wrapping sheet 3 of in the rear region $A_B$, and the upper layer adhesive 21 of the upper layer tape 4A that has been peeled from the lower layer substrate 22 is being exposed. As described above, when the individually wrapped sanitary napkin is opened, the upper layer tape 4A is peeled from the lower layer substrate 22, and the upper layer adhesive 21 of the upper layer tape 4A is exposed. Therefore, even if the adhesive force of the upper layer adhesive 21 of the upper layer tape 4A is increased, the wrapping sheet 3 can be smoothly unfolded without being torn. In addition, even in a post-process, a sufficient adhesion strength can be ensured by the exposed upper layer adhesive 21 of the upper layer tape 4A.

As illustrated in FIG. 7, the separating distance L1 between the lower layer adhesive 23 and the opening start end 14 is preferably 2 mm to 8 mm. The lower layer adhesive 23 can be securely prevented from adhering to the opening start end 14 by setting the separating distance between the lower layer adhesive 23 and the opening start end 14 to be at least 2 mm. If the separating distance L1 exceeds 8 mm, an effect of the adhesive tab tape 4 sealing the opening start end 14 would be reduced.

The length L2 to which a portion of the lower layer substrate 22 extends from the opening start end 14 to the surface of the folded portion in the front region $A_F$ is preferably 2 mm to 5 mm. The upper layer adhesive 21 can be securely prevented from adhering to the opening start end 14 by causing the portion of the lower layer substrate 22 to extend at least 2 mm from the opening start end 14. If the length L2 exceeds 5 mm, a portion of the upper layer tape 4A attached to the folded portion in the front region $A_F$ would be too far from the opening start end 14. Therefore, when the user opens the individually wrapped sanitary napkin N, the force to lift the upper layer tape 4A would not easily act on the folded portion of in the front region $A_F$, and thus, the individually wrapped sanitary napkin N would not be smoothly opened from the opening start end 14.

As described above, the extended portion 24 of the lower layer substrate 22 is provided as a non-adhesive portion of the adhesive tab tape 4, and extends a predetermined length from the opening start end 14 toward the front side and also extends a predetermined length from the opening start end 14 toward the rear side. Accordingly, the adhesive of the adhesive tab tape 4 does not adhere to the opening start end 14.

The length L3 to which the extended portion 25 of the upper layer tape 4A extends from the lower layer substrate 22 to the surface of the folded portion in the front region $A_F$ is preferably 10 mm to 30 mm. The length 3 is the length of a portion of the upper layer tape 4A that is attached to the wrapping sheet 3. The length 3 is required to lift the upper layer tape 4A and peel the folded portion in the front region $A_F$ from the opening start end 14 when the individually wrapped sanitary napkin N is opened.

As illustrated in FIG. 7, the upper layer tape 4A preferably includes a pinch portion 26. The pinch portion 26 is formed at the end, on the folded portion side in the rear region $A_B$, of the upper layer tape 4A, and extends beyond the lower layer tape 4B. The pinch portion 26 is non-adhesive and is not bonded to an underlying member. By providing the non-adhesive pinch portion 26 at the end of the upper layer tape 4A, the end of the upper layer tape 4A can be easily pinched and the individually wrapped sanitary napkin N can be smoothly opened. In order to form the non-adhesive pinch portion 26, the upper layer substrate 20 is caused to extend beyond the upper layer adhesive 21, and this extended portion of the upper layer adhesive 21 is folded downward along the edge of the upper layer adhesive 21 and is fixed to the lower surface of the upper layer adhesive 21, as illustrated in FIG. 7. Alternatively, in order to form the non-adhesive pinch portion 26, another member may be fixed to the lower surface of the upper layer adhesive 21, or no adhesive may be applied to a portion of the upper layer adhesive 21 where the pinch portion 26 is to be formed.

Figure 9:
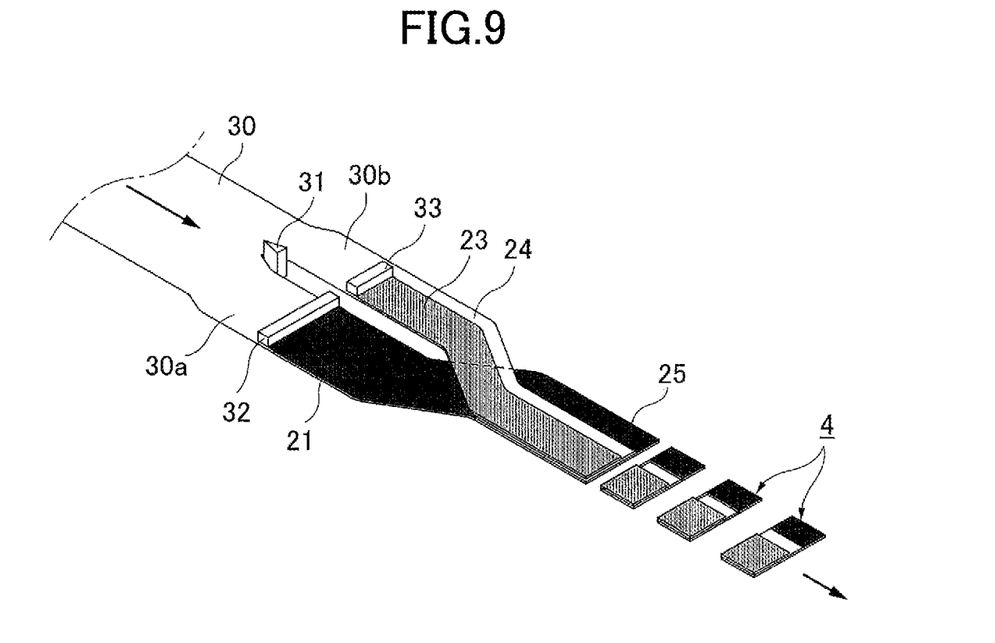
FIG. 9 is a perspective view illustrating a process for manufacturing the adhesive tab tape 4.

Next, a method for manufacturing the adhesive tab tape 4 will be described with reference to FIG. 9. A substrate sheet 30, having a width in which an upper layer substrate 20 and a lower layer substrate 22 are arranged continuously, is cut into an upper layer substrate sheet 30a and a lower layer substrate sheet 30b at a predetermined position in the widthwise direction by a cutter device 31. An adhesive applying device 32 applies an upper layer adhesive 21 to a predetermined area of the upper layer substrate sheet 30a. Further, an adhesive applying device 33 applies a lower layer adhesive 23 to a predetermined area of the lower layer substrate sheet 30b, while leaving a non-adhesive extended portion 24. Then, the upper layer substrate sheet 30a and the lower layer substrate sheet 30b are overlapped with each other and cut into an adhesive tab tape 4 having a predetermined width. For ease of understanding, the top and bottom of the adhesive tab tape 4 are reversed, that is, the lower layer adhesive 23 is exposed upward.

In a manufacturing apparatus described above, the width of the lower layer adhesive 23 applied to the lower layer substrate sheet 30b by the adhesive applying device 33 can be adjusted. Therefore, the extended portion 24 of the lower layer substrate 22, which is a non-adhesive portion, can be set to have any length. Accordingly, the adhesive tab tape 4 can be easily manufactured and the design of the adhesive tab tape 4 can be easily changed.

DESCRIPTION OF THE REFERENCE NUMERALS 1 sanitary napkin
2 peeling sheet
3 wrapping sheet
4 adhesive tab tape
5 back sheet 6 top sheet
7 absorbent body
8 side sheet
9 body displacement-preventing adhesive layer
10 wing displacement-preventing adhesive layer
11 body peeling sheet
12 wing peeling sheet
13 bonding portion
14 opening start end
15 side seal portion
20 upper layer substrate
21 upper layer adhesive
22 lower layer substrate
23 lower layer adhesive
24 extended portion of lower layer substrate 22
25 extended portion of upper layer tape 4A
26 pinch portion
30 substrate sheet
31 cutter device
32, 33 adhesive applying device

The invention claimed is:

1. An individually wrapped absorbent article comprising:
an absorbent article;
a wrapping sheet; and
an adhesive tab tape,
wherein, with the absorbent article being placed on the wrapping sheet, both end portions in a lengthwise direction of the wrapping sheet are folded toward a center of the wrapping sheet such that a first folded portion overlaps with a second folded portion different from the first folded portion and an end of the first folded portion serves as an opening start end, and the adhesive tab tape is attached to a surface of the first folded portion and a surface of the second folded portion,
wherein the adhesive tab tape includes an upper layer tape and a lower layer tape, the upper layer tape including an upper layer substrate and an upper layer adhesive that is applied to a lower surface of the upper layer substrate, and the lower layer tape being removably laminated on a lower side of the upper layer adhesive and including a lower layer substrate and a lower layer adhesive that is applied to a lower surface of the lower layer substrate,
wherein the lower layer adhesive of the lower layer tape is disposed on the surface of the second folded portion, and a portion of the lower layer substrate extends above the opening start end from the lower layer adhesive to the surface of the first folded portion, wherein the lower layer adhesive is free from being in direct contact with the first folded portion, and
wherein a portion of the upper layer tape, including the upper layer substrate and the upper layer adhesive, extends from the lower layer substrate to the surface of the first folded portion.

2. The individually wrapped absorbent article according to claim 1, wherein a separating distance between the lower layer adhesive and the opening start end is 2 mm to 8 mm.

3. The individually wrapped absorbent article according to claim 1, wherein a length to which a portion of the lower layer substrate extends from the opening start end to the surface of the first folded portion is 2 mm to 5 mm.

4. The individually wrapped absorbent article according to claim 1, wherein a length to which the portion of the upper layer tape extends from the lower layer substrate to the surface of the first folded portion is 10 mm to 30 mm.

5. The individually wrapped absorbent article according to claim 1, wherein an end, on the second folded portion, of the upper layer tape extends beyond the lower layer tape, and the end of the upper layer tape is non-adhesive.

* * * * *